Figure 1:
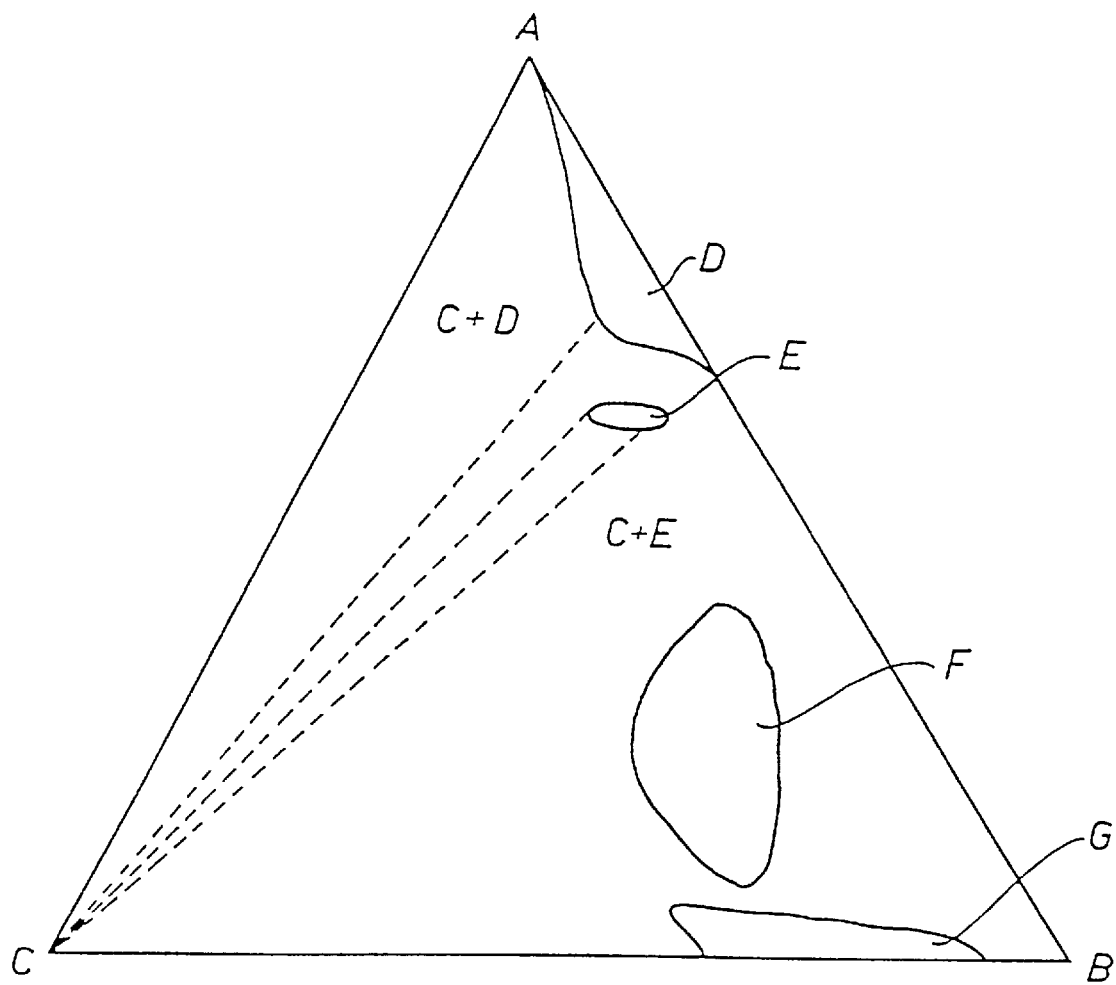

United States Patent [19]
Ljusberg-Wahren et al.

[11] Patent Number: 5,807,573
[45] Date of Patent: Sep. 15, 1998

[54] LIPID BASED COMPOSITION CONTAINING DIACYLGLYCEROL, PHOSPHOLIPID, POLAR LIQUID AND BIOLOGICALLY ACTIVE MATERIAL

[75] Inventors: Helena Ljusberg-Wahren, Höllviken; Kåre Larsson, Bjärred, both of Sweden

[73] Assignee: GS Development AB, Malmo, Sweden

[21] Appl. No.: 750,126
[22] PCT Filed: May 24, 1995
[86] PCT No.: PCT/SE95/00593
  § 371 Date: Nov. 27, 1996
  § 102(e) Date: Nov. 27, 1996
[87] PCT Pub. No.: WO95/34287
  PCT Pub. Date: Dec. 21, 1995

[30] Foreign Application Priority Data

Jun. 15, 1994 [SE] Sweden .................................. 9402106

[51] Int. Cl.[6] .................................................. A61K 37/00
[52] U.S. Cl. .......................................................... 424/450
[58] Field of Search .............................. 424/400; 264/4.1, 264/4.3

[56] References Cited

U.S. PATENT DOCUMENTS

| | | |
|---|---|---|
| 4,388,307 | 6/1983 | Cavanak . |
| 5,143,934 | 9/1992 | Lading et al. . |
| 5,151,272 | 9/1992 | Engstrom et al. . |
| 5,164,191 | 11/1992 | Tabibi ..................................... 424/450 |
| 5,196,201 | 3/1993 | Larsson et al. . |
| 5,262,164 | 11/1993 | Damani . |

FOREIGN PATENT DOCUMENTS

| | | |
|---|---|---|
| 0 314 689 | 5/1989 | European Pat. Off. . |
| 84/02076 | 6/1984 | WIPO . |
| 92/20377 | 11/1992 | WIPO . |

OTHER PUBLICATIONS

Biochemistry, vol. 29, 1990, John M. Seddon, "An Inverse Face–Centered Cubic Phase Formed by Diacylglycerol–Phosphatidylcholine Mixtures", p. 7997.

"Lipid Polymorphism: A Correction. The structure of the Cubic Phase of Extinction Symbol Fd—Consists of Two Types of Disjointed Reverse Micelles Embedded in a Three–Dimensional Hydrocarbon Matrix", Vittorio Luzzati et al., *Biochemistry*, 1992, 31, pp. 279–285.

"Formulation of a Drug Delivery System Based on a Mixture of Monoglycerides and Triglycerides for Use in Treatment of Periodontal Disease", Tomas Norling et al., *J. Clin. Periodontal*, 1992, 19, pp. 687–692.

*Primary Examiner*—Gollamudi S. Kishore
*Attorney, Agent, or Firm*—Burns, Doane, Swecker & Mathis, L.L.P.

[57] ABSTRACT

A biologically active composition containing (a) a diacyl glycerol, (b) a phospholipid and, optionally, (c) a polar liquid in such proportions that they together form an L2-phase or a cubic liquid crystalline phase, in which a biologically active material is dissolved or dispersed. A method for preparing the composition by mixing (a), (b) and, optionally, (c) for forming an L2-phase or a cubic liquid crystalline phase, the biologically active material being added before, during or after the formation of said phase. Use of the L2-phase or the cubic liquid crystalline phase for encapsulating a biologically active material for obtaining a preparation is provided, which yields a controlled release of the biologically active material.

29 Claims, 1 Drawing Sheet

LIPID BASED COMPOSITION CONTAINING DIACYLGLYCEROL, PHOSPHOLIPID, POLAR LIQUID AND BIOLOGICALLY ACTIVE MATERIAL

This application is a 3717 PCT/SEQS /00593 filed May 24, 1995.

TECHNICAL FIELD

The present invention relates to the field of polar lipids and, more specifically, to a new biologically active composition, which is based on polar lipids and has been found to yield significant improvements as compared with previously known lipid-based compositions used as carriers for biologically active materials. More concretely, the invention relates to a new composition whose L2-phase and cubic liquid crystalline phase each confer advantages in the controlled release of biologically active material encapsulated therein, as compared with previously known, similar L2-phases and cubic phases, respectively, and are mutually positioned in a phase diagram so as to also confer valuable advantages for some specific applications in which special demands are placed on the release of biologically active materials.

BACKGROUND OF THE INVENTION

Polar lipids are amphiphilic molecules, i.e. they are both "hydrophilic" and "hydrophobic". When placed in an aqueous solution, they must thus unite in some way or another to form different kinds of aggregates. The most well-known of the aggregates formed in water is probably the spheric micelle, which typically contains 50–100 lipid molecules arranged in such a manner that their hydrocarbon tails (the hydrophobic part) form the interior of the micelle concerned and the polar main groups (the hydrophilic part) act as a shield against the surrounding water.

The micelle, however, is only- one of many different types of aggregate formed. It is also possible to find both bar-shaped micelles and reversed-type micelles (L2), which are also called microemulsions in which water forms the internal phase.

A number of liquid crystalline structures are also normally found in systems of polar lipid and water. These comprise hexagonal phases of the normal type (HI) and of the reversed type (HII), as well as the lamellar phase (Lα). The lamellar structure provides, at an excess of water, liposomes, which are spheroidal shells of lipid bilayers. These have been studied to a very large extent and have been used in the release of pharmaceutical preparations, for example in chemotherapy of cancer. The first liposome product on the market contains amphoteracin and is intended for treatment of infections.

Many cubic crystalline phases are said to be both water- and oil-continuous, i.e. bicontinuous. These phases consist of lipid bilayers whose centre forms a minimum surface, separating two water channel systems. There are four main positions in the phase diagram, in which cubic phases can be found. Cubic phases of normal topology (oil-in-water) can be found either adjacent the micellar solution (in many cases between the normal micellar solution (L1) and the hexagonal HI-phases), or between the HI-phase and the lamellar Lα-phase. In the first-mentioned case, the structures are considered to be anisotropic micellar aggregates. In the last-mentioned case, the structures seem to be permanently bicontinuous. Cubic phases may also be found between the Lα- and the HII-phase. In this case, the structures are also bicontinuous. Cubic liquid crystalline phases occurring in the fourth possible position in the phase diagram, i.e. between the HII-phase and the reverse micellar solution (L2), have been studied by J. M. Seddon in Biochemistry, Vol. 29, No. 34, 1990, pp 7997–8002, and by V. Luzzati et al, in Biochemistry 1992, 31, pp 279–285, but these articles do not concern the properties which these phases have been found to possess in the release of biologically active materials.

Furthermore, certain compositions are per se known, whose L2-phase, hexagonal phase and/or cubic phase (formed when mixing water and amphiphilic lipids) have been used for the release of biologically active materials. As examples of publications illustrating this, mentioned can be made of U.S. Pat. No. 4,388,307, U.S. Pat. No. 5,143,934, U.S. Pat. No. 5,151,272, U.S. Pat. No. 5,196,201, U.S. Pat. No. 5,262,164, EP,B1, 314,689, WO 92/20377 and the article by T. Norling et al. in J. Clin. Periodontol 1992, 19, pp 687–692. This does not correspond to the composition of the L2-phase and the cubic phase for the composition according to the present invention, the mutual positioning of the two phases or their advantageous properties in the controlled release of biologically active materials.

SUMMARY OF THE INVENTION

According to the present invention, a new composition is provided, which is so made up and has such properties that there are a number of advantages as compared with the previously known compositions within this field. Thus, it has surprisingly been found that the biocompatibility of a composition according to the invention is better than that of the previously known compositions of this type based on monoglycerides (monoacyl glycerol). Besides it has been unexpectedly found that the release profile of the biologically active material from the composition according to the present invention is more advantageous than that of the previously known glyceride-based compositions used for this purpose. In addition to this, the L2-phase and the cubic phase have such a mutual positioning in a phase diagram that the L2-phase may be used for specific applications of a biologically active material in situ in mammals, especially humans, by the L2-phase swelling when contacting body fluid or added polar liquid, such that a phase transition to the corresponding cubic liquid crystalline phase occurs. In practice, this means that a casting in situ can be accomplished in the specific position in which the application of the biologically active material is desired.

A first object of the invention thus is to provide a lipid composition, which yields a controlled release of a biologically active material encapsulated therein.

A further object of the invention is to provide a lipid composition, Which has improved biocompatibility compared with previously known glyceride-based systems.

One more object of the invention is to provide a composition, which yields an enhanced release profile for a biologically active material as compared with previously known monoacyl-glycerol-based systems.

One more object is to provide a lipid composition, in which the carrier of the biologically active material is biodegradable.

A still further object of the invention is to provide a lipid composition, for which the phase transition from the L2-phase to the cubic liquid crystalline phase can be used to "cast" the desired biologically active material in situ where the intended effect should occur.

Other objects and advantages of the invention will be apparent to those skilled in the art from the following, detailed description of the invention.

The objects of the invention are achieved by a glycerol-ester-based composition comprising (a) at least one diacyl glycerol, wherein the acyl groups, which are the same or different, are each derived from an unsaturated fatty acid having 16–22 carbon atoms, or from a saturated fatty acid having 8–10 carbon atoms, (b) at least one phospholipid selected from glycerophophatides and sphingophosphatides, wherein the acyl groups, which are the same or different, are each derived from a fatty acid having 14–22 carbon atoms, and optionally, (c) at least one polar liquid selected from the group consisting of water, glycerol, ethylene glycol and propylene glycol, the proportions between the components (a), (b) and optionally (c) being such that they together form an L2-phase or a cubic liquid crystalline phase, wherein (c) is an optional component in the case of L2-phase and a requisite component in the case of cubic liquid crystalline phase, and the biologically active material being dissolved or dispersed in said L2-phase or said cubic liquid crystalline phase.

In general, the unsaturated fatty acid for the diacyl glycerol (a) should be liquid at room temperature and it should preferably contain 16–20 carbon atoms. A particularly advantageous fatty acid in this context is one having 18 carbon atoms. Of these fatty acids having 18 carbon atoms, oleic acid and linolic acid are of special interest, and oleic acid is the one most preferred. Diacyl glycerol (a) from saturated fatty acids in liquid state implies, however, that the chain length of the fatty acid is shorter, for example 8 or 10 carbon atoms. So-called medium chain length triglycerides may be used as starting material for the preparation.

In many cases it is, however, not necessary to use or even, if anything, preferred from the economical point of view not to use the diacyl glycerol in pure or synthesised form, but to use a natural product containing essentially the same, for example in which the desired diacyl glycerol is obtained by esterification/reesterification between glycerol and vegetable or animal oils or fatty acids therefrom. Preferred examples of such oils are canola, maize, cottonseed, olive, rape-seed, soybean, safflower, sunflower, linseed and tall oil.

The used phospholipid is, as mentioned above, generally based on a fatty acid having 14–22 carbon atoms. A preferred carbon atom content of said fatty acid is, however, 16–20, while 16 or 18 carbon atoms are especially preferred. Also in this case, a phospholipid derived from a natural product in the form of vegetable or animal raw materials may, however, also be concerned. Examples of preferred such raw materials are soybean, rape-seed and egg.

However, the phospholipid may of course also be an entirely synthetic product.

As preferred examples of glycerophosphatides, mention can be made of lecithines and cephalines which are based on choline and, respectively, ethanolamine or serine. Especially preferred is phosphatidyl choline. An especially preferred sphingophosphatide is sphingomyelin which is also based on choline. Specific examples of phospholipids are dioleylphosphatidyl choline and dioleylphosphatidyl ethanolamine.

In respect of the unsaturated fatty acid for the diacyl glycerol (a), the term "unsaturated" includes both monounsaturated and polyunsaturated, i.e. said acid can contain one or more unsaturated valences.

The fatty acid for the phospholid (b) can be saturated, monounsaturated and/or polyunsaturated. A saturated fatty acid of special interest is one having 16 carbon atoms, while a monounsaturated fatty acid of special interest is one having 18 carbon atoms.

The polar liquid used in the inventive composition is preferably water, but this water may also be wholly or partially replaced with another polar liquid, such as glycerol, ethylene glycol and/or propylene glycol. The release rate of the biologically active material may thus be, for example, adjusted by varying the proportions of the used polar liquids. By water is meant not only pure water, but of course also, for instance, an isotonic aqueous solution or a body fluid, especially in the case of casting in situ in or on the tissue of humans or animals.

The exact composition of the L2-phase and/or the cubic liquid crystalline phase is, of course, taken from a phase diagram, and the desired release rate of the biologically active material which is to be encapsulated is readily determined by a person skilled in the art by simple routine testing. The enclosed FIGURE illustrates, as will be described in more detail below, the phase diagram for a specific system within the scope of the present invention, which means that the exact composition of the L2-phase and/or the cubic phase can be taken from this diagram for exactly this specific system. Since the inventive idea has now been presented, the expert will probably have no difficulties in preparing the corresponding phase diagram for other specific systems within the scope of the invention and determining the exact position of the desired L2-phase and/or cubic phase.

However, it may be generally said that the weight ratio of diacyl glycerol:phosphatidyl choline is in the range from 95:5 to 50:50, preferably from 90:10 to 70:30.

The weight content of the polar liquid (c), based on the total weight of (a) plus (b) plus (c), is generally in the range of 0–20%, especially 0–15%, such as 0–10% for the L2-phase and 5–15% for the cubic phase. Thus, in the case of L2-phase, the content of the polar liquid (c) may even be 0, i.e. even the diacyl glycerol and the phospholipid mixed together may give the desired L2-phase. In many cases, it is however the matter of a certain content of polar liquid in the L2-phase, and in the cubic liquid crystalline phase, said liquid is of course always present. Small amounts of water may also be bound to the phospholipid and, thus, be added via the phospholipid.

As indicated above, an especially preferred embodiment of the inventive composition is represented by the case in which the cubic liquid crystalline phase is obtained by swelling of the corresponding L2-phase with the polar liquid. Of course, this means in such a case that the L2-composition is selected such that the adding of the stated liquid, e.g. body fluid, yields a phase transition from the L2-phase to the cubic liquid crystalline phase. Other phase transitions are, however, also within the scope of the invention, if desired. In some cases, a reversed hexagonal chase can be formed in addition to the cubic phase.

By the above-mentioned phase transition, the cubic liquid crystalline phase can be cast in situ where the desired controlled release of the biologically active material is wanted. The enormous advantages this may confer in some specific cases for application of special medical preparations for achieving, for instance, a local effect, will be easily understood by the expert.

The invention is not restricted to one or a few specific biologically active materials, but is generally applicable to the different types of biologically active materials which have been present earlier in similar contexts. However, it will be easily realised that new fields of application for certain types of medical preparations will open up by means of the present invention, especially when using the phase transition L2 to cubic phase. By "biologically active material" or the like is, in the present case, like before, meant a compound or composition which, when present in an effective amount, reacts with and/or affects living cells and organisms. This includes also a biological material which requires a controlled release for vaccination purposes. Preventing the release of medicals having a bad taste is a further application of the invention.

An interesting group of compounds for encapsulation according to the present invention is, however, the group of pharmaceutical compounds, such as antibiotics, antimycotics, proteins, peptides, steroids, local anesthetics, chemotherapeutants and antiviral substances.

Whether the biologically active material is dissolved or dispersed depends, of course, on its solubility in the phase mentioned, i.e. whether it is water-soluble, lipid-soluble etc, but to this part of the invention, the prior art technique applies, as well as to where in the chase concerned the resolution/dispersion takes place in reality.

The content of the biologically active material is of course dependent on a number of different factors which are well-known to the expert, especially the desired degree of activity. The content must therefore be determined by the expert in each individual case. However, it may be generally said that the biologically active material is present in an amount of 0.01–30%, especially 0.1–5% for soluble substances, and 5–30% for a dispersion, the percentages being expressed as percent by weight based on the weight of the total composition.

The biologically active composition is, as indicated above, of special interest as pharmaceutically acceptable composition. Of course, this also means that it is prepared in a conventional manner for the desired administration.

Examples of specific applications in which the biologically active composition according to the present invention may be used are when administering antibiotics (e.g. tetracycline, metronidazole), for example when treating parodontosis;

for enhancing the absorption of proteins/peptides (e.g. cyclosporins);

when treating infections in and adjacent mucous membranes;

in parenteral administration of drugs, especially via the L2-phase (for example vaccine), and in depot preparation for e.g. steroids or antibiotics.

However, these applications are in no way restrictive to the invention, since this is primarily directed to new carriers for active substances, and not to the substances as such.

According to another aspect of the invention, a method is provided for preparing the above described composition, the method comprising the steps of mixing the diacyl glycerol (a), the phospholipid (b) and, optionally, the polar liquid (c) in such amounts that an L2-phase, alternatively a cubic liquid crystalline phase, is formed, the mixing procedure for providing said L2-phase or said cubic liquid crystalline phase occurring according to per se known principles, which need not be described here.

The addition of the biologically active material is carried out before, during or after the formation of said L2-phase or said cubic liquid crystalline phase. Regarding the addition of the active material to said phase "before" the formation thereof, it should also be said for the sake of clarity that this means of course that the material can be added from the beginning to one of the components (a), (b) or (c), before they are in turn mixed for obtaining the desired L2-phase or cubic phase.

Besides, according to that described above, the cubic liquid crystalline phase is possibly formed in the position in which the controlled release of the biologically active material is desired, viz. by the presence or addition of the polar liquid (c), for example in the form of body fluid.

Moreover, the preferred embodiments which have been described above in connection with the inventive composition apply to the method according to the invention.

Finally, the invention also relates to the use of an L2-phase or a cubic liquid crystalline phase according to the above definitions for encapsulating a biologically active material for obtaining a preparation, which yields a controlled release of the biologically active material. Such a preparation can also imply that the lipid-based composition is dispersed in an aqueous solution by prior art technique.

Also in respect of the use, the preferred embodiments are those described in more detail above.

It may also be added that in the present case, the term "biocompatibility" has the generally recognised meaning ability of a material to give a biologically acceptable, or good, response in a host organism in a specific application. More concretely, the lipid mixture must not cause undesirable tissue reactions in the form of infection, inflammation or other rejection phenomena. Examples of undesirable reactions are swelling, pain or the formation of connective tissue capsules. It is also important that the lipid mixture affects the inherent healing power as little as possible, i.e. such that the natural healing process is not disturbed or affected to any decisive degree.

A BRIEF DESCRIPTION OF THE DRAWING

The enclosed FIGURE illustrates a ternary diagram of the specific system diacyl glycerol from sunflower oil, phosphatidyl choline from soybean and water at 25° C. In this drawing FIGURE, the symbols have the following meanings:

A=diacyl glycerol

B=phospholipid

C=polar liquid

D=L2-phase, and

E=cubic liquid crystalline phase.

Moreover, this phase diagram shows:

F=hexagonal, and

G=lamellar liquid crystalline phase.

EXAMPLES

The present invention will finally be further illustrated by means of the following working examples regarding the preparation of some specific compositions according to the invention and their properties in the release of biologically active material.

EXAMPLE 1

Phospholipid in the form of a purified soybean phosphatidyl choline (about 95%) and diacyl glycerol derived from sunflower oil and containing 80% oleic acid, based on the total fatty acid content, were weighed in the ratio of 15:85 in an injection bottle (10 ml), which was filled with inert atmosphere and sealed. The sample was allowed to assume equilibrium at room temperature and was centrifuged back and forth, thereby providing a homogeneous mixture of the components. The L2-phase was formed in the form of a homogeneous, mobile oil.

EXAMPLE 2

1 g of the L2-phase prepared according to Example 1 above was transferred to a test tube, which was centrifuged such that all the material was obtained on the bottom. 9 g of an aqueous solution of Pluronic F68 (1.1 weight/weight BASF) were added to the test tube. The sample was created with an ultrasonic rod (Branson sonifier 250, microtip) for 1+2 min at a power of 52 W+56 W. A stable, milky emulsion was formed in this treatment of the two phases in the sample.

EXAMPLE 3

A fine-grain powder of metronidazol benzoate (7% by weight) was mixed with the L2-phase prepared from the above-mentioned phosphatidyl choline and diacyl glycerol in the ratio of 3:7. The dispersion was of relatively low viscosity, but when adding water to the dispersion, the sample solidified.

The particle dispersion of metronidazol benzoate in the L2-phase was studied under microscope, magnified 200 times. This study showed that the particles were well dispersed without any formation of aggregates.

EXAMPLE 4

The biocompatibility and the biodegradability of liquid crystalline phases, which may function as depot preparations for drugs, were studied in a so-called abdomen plug model on rat. The model is developed for testing implant material, for example plastics, but has also appeared to function satisfactorily for the evaluating of depot preparations. This model means that the material to be studied is inserted between the straight abdominal muscle and the peritoneum in male rats (Sprague-Dawley, 350–400 g).

The samples studied were obtained from soybean phosphatidyl choline and sunflower oil glycerides. The lipids were first swelled with a physiological salt solution to liquid crystalline phases, which were implanted. These liquid crystalline phases can be in equivalence with an excess of water and are suitable for testing in this model.

The animals were put to death after 10 and 30 days, and the size of the connective tissue capsule and the amount of residual sample were noted.

The thickness of the capsule may be taken as a measure of the biocompatibility of the material. The results after 10 days are summarised in the table below. The measure of the capsule thickness is relative and concerns the number of squares in the microscope.

After 30 days, all lipid implants had decreased in size or disappeared completely, which proves that the lipids are biodegradable.

| Lipid | Capsule thickness |
|---|---|
| monoacyl glycerol | 2.0 |
| phospholipid/diacyl glycerol 1:1 | 0.4* |

*the capsule was partly fragmented

EXAMPLE 5

Biodegradable systems for the controlled release of bioactive systems should have a degradation profile which conforms with the release, since otherwise an empty carrier, which serves no purpose, may remain in the tissue. This is especially the case with water-soluble substances, which are released by diffusion. Therefore, a study was made of the effect of water on particles of a water-soluble colourant (methylene blue) which was dispersed in two different lipid carrier systems.

Particles of methylene blue were thus mixed with two different L2-phases, viz. a first one from the system monoacyl glycerol (sunflower oil)/water and a second one from the system phospholipid/diacyl glycerol from Example 3. Both L2-phases formed a highly viscous cubic liquid crystalline phase at an excess of water. In the first case, the cubic phase was both water- and oil-continuous, whereas the cubic phase formed in the latter case was oil-continuous only.

The samples were studied under microscope, magnified 200 times, after addition of water, and the following phenomena were noted:

a distinct release of methylene blue from the dispersion to water occurred from the monoacyl-glycerol-based system. The dispersion of methylene blue in the L2-phase of diacyl glycerol/phospholipid demonstrated no such release, when an excess of water was present.

The release of drugs from the system phospholipid/diacyl glycerol can, consequently, be assumed to be controlled more by the degradation shown in vivo in Example 4 than by diffusion, whereas the release of drugs from a liquid crystalline phase based on monoglyceride will be more difficult to control, since this is more dependent on the properties of the pharmaceutical preparation, such as molecular size and solubility.

EXAMPLE 6

In this example a dispersion of a local anesthetic was prepared by dispersing a fine powder of lidocaine hydrochloride in a liquid 33:67 mixture of phosphatidyl choline from soy and diacyl glycerol from tall oil to an L2-phase containing 40% by weight of lidocaine-HCl. The dispersion was relatively mobile and was sprayable. The preparation solidified when sprayed into water and a sustained dissolution of the lidocaine-HCl crystals was obtained as compared with the case when said crystals were directly mixed with water.

EXAMPLE 7

Cytotoxity tests were performed in the following way. Two liquid crystalline phases having cubic structures but different compositions were tested in a way that is utilized in the biomaterial field (ISO 109935:1992(E)) to test whether plastic materials release anything that is toxic to cells. Both these cubic phases can be in equilibrium with water without being dispersed and can thus be tested as solid bodies.

Samples from the cubic phases having an area of 3,14 $cm^2$ were contacted with water (4 ml) at 37° C. for more than 24 hours. The aqueous phase was then separated from the cubic phase and admixed with growth media to which a cell culture was added. The evaluation was then performed with reference to growth inhibition of fibroblasts. The results were as follows:

| Composition of cubic phase | | Growth inhibition |
|---|---|---|
| Monoolein* from tall oil | 65% | Yes |
| Water | 35% | |
| Diolein* from tall oil | 60% | No |
| Phosphatidicyl choline from soy | 30% | |
| Water | 10% | |

*Purified by molecular distillation

We claim:

1. A biologically active composition which is glycerol-ester-based containing
   (a) at least one diacyl glycerol, wherein the acyl groups, which are the same or different, are each derived from an unsaturated fatty acid having 16–22 carbon atoms, or from a saturated fatty acid having 8–10 carbon atoms,
   (b) at least one phospholipid selected from glycerophosphatides and sphingophosphatides, wherein the acyl groups, which are the same or different, are each derived from a fatty acid having 14–22 carbon atoms, and optionally,
   (c) at least one polar liquid selected from the group consisting of water, glycerol, ethylene glycol and propylene glycol, the proportions between the components (a), (b) and optionally (c) being such that they together form an L2-phase or a cubic liquid crystalline phase, wherein (c) is an optional component in the case of L2-phase and a requisite component in the case of cubic liquid crystalline phase, and
   (d) a biologically active material being dissolved or dispersed in said L2-phase or said cubic liquid crystalline phase.

2. The composition as claimed in claim 1, wherein the fatty acid from which the diacyl glycerol (a) is derived, is an unsaturated fatty acid having 18 carbon atoms.

3. The composition as claimed in claim 1, wherein the fatty acid from which the phospholipid (b) is derived, is a fatty acid having 16 or 18 carbon atoms, or a monounsaturated fatty acid having 18 carbon atoms.

4. The composition as claimed in claim 2, wherein the fatty acid is selected from the group consisting of oleic acid and linoleic acid, preferably oleic acid.

5. The composition as claimed in claim 1, wherein the unsaturated fatty acid for the diacyl glycerol (a) is obtained from an oil selected from the group consisting of canola, maize, cottonseed, olive, rape-seed, soybean, safflower, sunflower, linseed and tall oil.

6. The composition as claimed in claim 1, wherein the glycerophosphatide is selected from the group of lecithines and cephalines.

7. The composition as claimed in claim 6, wherein the glycerophosphatide is phosphatidyl choline.

8. The composition as claimed in claim 1, wherein the phospholipid is derived from soybean, rape-seed or yolk.

9. The composition as claimed in claim 1, wherein the sphingophosphatide is sphingomyelin.

10. The composition as claimed in claim 1, wherein the polar liquid is water.

11. The composition as claimed in claim 1, wherein the weight ratio of diacyl glycerol:phospholipid is in the range from 95:5 to 50:50, preferably from 90:10 to 70:30.

12. The composition as claimed in claim 1, wherein the weight content of the polar liquid (c), based on the total weight of (a) plus (b) plus (c), is in the range of 0–20% by weight for the L2-phase and 5–15% by weight for the cubic liquid crystalline phase.

13. The composition as claimed in claim 1, wherein the proportions between the components (a), (b) and (c) are selected such that a cubic liquid crystalline phase is obtained, wherein the cubic liquid crystalline phase is obtained by swelling of the corresponding L2-phase with the polar liquid selected from the group consisting of water glycerol, ethylene glycol and propylene glycol.

14. The composition as claimed in claim 1, wherein the L2-phase and/or the cubic liquid crystalline phase is the phase (phases) as defined in the phase diagram in FIG. 1, where A represents diacyl glycerol from sunflower oil, B represents phosphatidyl choline from soybean and C represents water.

15. The composition as claimed in claim 1, wherein the biologically active material is selected from the group consisting of pharmaceutical compounds, such as antibiotics, antimycotics, proteins, peptides, steroids, local anesthetics, chemotherapeutants and antiviral substances.

16. The composition as claimed in claim 1, wherein the biologically active material is present in an amount of 0.01–30% by weight, based of the weight of the total composition, for soluble materials and 5–30% by weight for a dispersion of said materials.

17. A method for preparing a biologically active composition as claimed in claim 1, comprising mixing the diacyl glycerol (a), the phospholipid (b) and, optionally, the polar liquid (c) in amounts that provide for an L2-phase, or a cubic liquid crystalline phase to be formed, and dissolving or dispersing the biologically active material in the L2-phase and/or the cubic liquid crystalline phase before, during or after the formation of said L2-phase or cubic phase.

18. The method as claimed in claim 17, which comprises forming the cubic liquid crystalline phase in the position in which the controlled release of the biologically active material is desired, by the presence or addition of the polar liquid (c) in said position.

19. The method as claimed in claim 18, wherein the cubic liquid crystalline phase is formed by the addition of a body fluid.

20. A method of providing for the controlled release of a desired biologically active material comprising administering an L2-phase or a cubic liquid crystalline phase produced according to claim 1, which comprises an encapsulated biologically active material.

21. The method of claim 20, wherein the biologically active material is a protein or peptide.

22. The method of claim 20, which is used for the delivery of a biologically active material to a mucous membrane.

23. The method of claim 20, wherein the method is used for the treatment of paradentosis.

24. The method of claim 20, wherein the biologically active material confers immunity.

25. The composition of claim 3, wherein the fatty acid is a saturated fatty acid having 16 carbon atoms.

26. The composition of claim 11, wherein said weight ratio ranges from 90:10 to 70:30.

27. The composition of claim 12, wherein said weight content of the polar liquid (c) ranges from 0–15% by weight.

28. The composition of claim 27, wherein said weight content ranges from 0–10% by weight.

29. The composition of claim 16, wherein the biologically active material constitutes 0.1 to 5% by weight of the soluble materials obtained in said composition.

* * * * *